Figure 1:
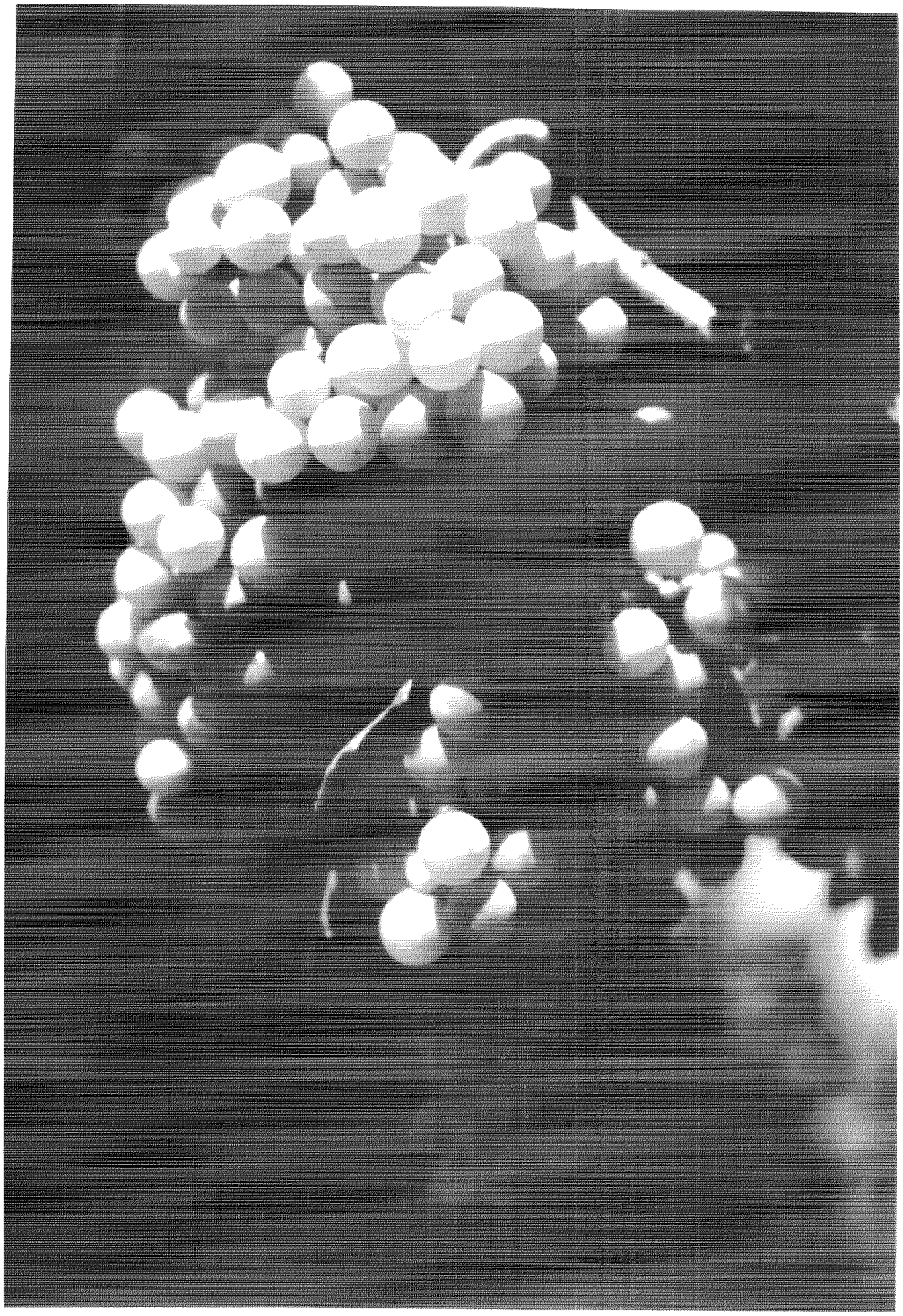

United States Patent [19]

Olmo

[11] Plant 5,013

[45] Mar. 29, 1983

[54] GRAPEVINE 'SYMPHONY'

[75] Inventor: Harold P. Olmo, Davis, Calif.

[73] Assignee: The Regents of the University of California, Berkeley, Calif.

[21] Appl. No.: 301,910

[22] Filed: Dec. 23, 1981

[51] Int. Cl.[3] ..... A01H 5/00

[52] U.S. Cl. ..... Plt./47

[58] Field of Search ..... Plt./47

*Primary Examiner*—James R. Feyrer

*Attorney, Agent, or Firm*—Townsend and Townsend

[57] ABSTRACT

A new and distinct variety of grapevine of the *vinifera* species, named 'Symphony', having the ability to produce either a light and dry white table wine characterized by a delicate Muscat-type aroma and flavor when harvested before full maturity or a natural sweet wine when picked more mature. The wine is very slow to oxidize and retains its typical aroma and flavor even after long periods of aging. The usual bitterness associated with Muscat-type varieties made as dry wines is not evident in the new variety.

2 Drawing Figures

1

This invention relates to a new and distinct variety of grapevine of the *vinifera* species, of the denomination 'Symphony' to be used for the production of white table or dessert wine, with a distinct and lasting Muscat aroma and flavor. Unlike most Muscat varieties, it can be produced as a light dry wine without traces of bitterness. The flavor and aroma are developed before full maturity of the fruit and by picking early, flavorful wines of low alcohol content can be produced easily which are now in great demand commercially, referred to as "light" or "soft" wines. Today's wine consumers prefer distinctive wines of varietal character that they can recognize.

In the drawings:

FIG. 1 illustrates typical clusters of the new variety and

Figure 2:
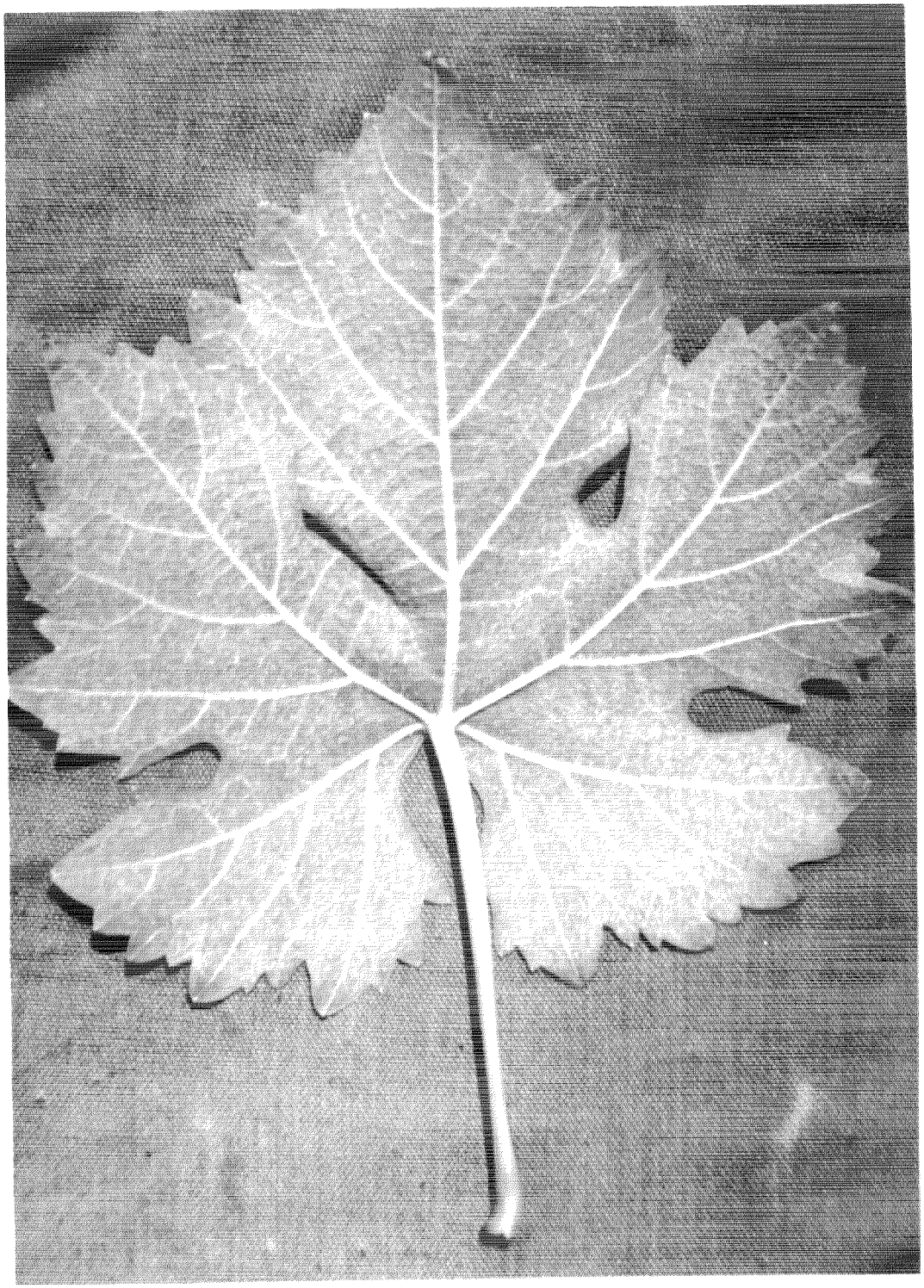

FIG. 2 demonstrates the leaf form and underside hairiness of the new variety.

This new variety is a result of a planned cross between "Grenache gris"×"Muscat of Alexandria," made May 21, 1940 at the University of California vineyard at Davis. A progeny of 94 seedlings were grown to fruiting and mini-samples of wine were produced for two seasons, in 1948 and 1949. The selection J5-58 proved to be a consistently high producer and scored above average as a natural sweet dessert wine, with a mild but pleasing Muscat character. The seedling vine first fruited in 1945, and yielded good crops with high sugar content, 25.0 Brix, and 0.50 acidity (as tartaric) when harvested the first week of October.

The original seedling vine was multiplied asexually in August 1958 by budding 2 plots of 12 vines each on the rootstock *rupestris* St. George (du Lot) at the Oakville Trial block located in Napa County, under the selection numbers 919 and 923. This was to test its performance in a cool table-wine growing region. Three other Muscat-type selections were in the same block. The newly propagated vines retained the same growth and fruiting habits of the original. Larger wine samples (5 gallons) were first produced in 1960 and annually thereafter until the trial was terminated in 1967. In 1971 the vine was also reproduced by cuttings at the Kearney Horticultural Field Station, Parlier, Calif., to test its performance in a hot climatic zone, identified as selection 250 F. The progeny vines thus grown retained all the characteristics of the original. Production and wine trials followed in 1970. The wines produced from both locations again had the typical flavor and aroma that distinguish it.

2

During the trials, observations of the must and wine uncovered an important attribute. Bottled wine samples after 10 years in the cellar have maintained good color, flavor and aroma. Persistence of the Muscat aroma and flavor is not a common event in aged table wines of varieties with Muscat character such as White Riesling.

The varietal characteristics of the novel plant are described below in detail. The color terminology is in accordance with Nickerson Color Fan, Munsell Color Co., Baltimore, Md.

*Vine.*—Vigorous and semi-upright, with some dormant canes often bunched together by interlacing tendrils, foliage canopy dense and shading fruit clusters, budding out several days after Thompson Seedless, senescent buds fruitful, showing good crop recovery after spring frost, no particular resistance has been noted to the common diseases and insects attacking the *vinifera* vine in California.

*Shoot tip* (12" to 14").—Very straight, erect, not leafy, young leaves slow in unfolding, white wooly with faint pink margins, tendrils prominent and much branched, often trifid; inflorescences large, apex dark red, florets very small and slow to enlarge, borne at nodes 2 and 3; first flat leaf deeply incised and five-lobed, central lobe elongated, green, dorsal side with loose long wooly hairs, but not floccose.

*Shoot.*—With larger longitudinal striations of maroon color, basal internodes very short, slow to elongate, resistant to detachment by wind, forms many short but persistent laterals, nodes very prominent and offset, tendrils numerous and persistent, much branched, slender and wiry, firmly attached and coiled to support.

*Cane.*—The canes are few in number, with very short internodes at the base, clusters borne on nodes 2 and 3, thus crowding and causing some displacement of the fruit; nodes flattened with well marked diaphragm and large leaf scars, eyes large, practically all are fruitful, flattened, well sealed by scales, and offsetting the woody and persistent laterals and protruding from their base, internodes having uniformly and finely striated fibers; pith solid, woody cylinder very tough and fibrous. Under good growing conditions the terminal portions of the canes fail to mature and show considerable dieback, like the Grenache parent.

*Leaf.*—Upper surface moderate olive green 5G/Y 4/3, distinctly 5-lobed, terminal lobe protruding beyond marginal outline, upper (major) lateral sinuses deep, with lobes overlapping to form closed eyelets; lower sinuses open and V-shaped; petiolar sinus narrow, open, lyre-shaped; teeth large, obtuse; lobes terminating in two large apical teeth of about equal size; lower leaf surface covered with uniform dense grey indument, not becoming floccose; petiole slender, slightly shorter than midrib.

*Cluster.*—Usually two per shoot, at nodes 2 and 3, primary (basal) one 14.9×17.8 cm, avg. 372 gm., basal segment of peduncle very short, 1 cm, very thick 3 to 6 mm, woody only at point of attachment, difficult to locate and harvest with hand shears. From bend of basal peduncle segment to first fruiting branch 3 cm. Cluster form variable due to shoulder or wing, 190 seeded berries avg. on main rachis plus 38 small round seedless shot berries; wing on most cls. with about 25 berries plus a few shot berries. Fresh weight of rachis 9.3 gm, range 4 to 13 gm. Cluster compact to very compact, sometimes causing rupture of internal berries and leading to juice escape and spoilage. Berry spherical, wt. of ten largest per cluster 33 gm, range 26 to 41 gm; strong yellow green 5GY 6/8 to 5GY 7/10; skin thick with medium bloom, dull in appearance; flesh soft, juicy, but not gelatinous, juice clear, mild Muscat flavor; seeds usually 3 or 4 per berry, small, with pointed beak.

Yields range from 7 to 9 tons in the Central Valley and 5 to 6 tons in the unirrigated coastal districts.

Commercial harvest for dry table wine is in mid-September at Oakville, Napa County composition of must 20.0° Brix, acid (as tartaric) 0.75, and pH 3.3; near Fresno, Calif. harvest is in early September; Brix 20.6°, acid 0.60 and pH 3.5. For natural sweet wine, Brix of 22° or 23° is desirable. Low alcohol wines have been made using grapes of 17° to 18° Brix with higher acidity, still achieving excellent aroma and flavor.

I claim:

1. The new and distinct variety of grapevine herein described and illustrated and identified by the characteristics enumerated above.

* * * * *